United States Patent [19]

Viscovich

[11] Patent Number: 4,955,004
[45] Date of Patent: Sep. 4, 1990

[54] LIQUID ACOUSTIC WAVEGUIDE TUBE

[75] Inventor: Paul W. Viscovich, Longwood, Fla.

[73] Assignee: Westinghouse Electric Corp., Pittsburgh, Pa.

[21] Appl. No.: 240,779

[22] Filed: Sep. 6, 1988

[51] Int. Cl.$^5$ .............................................. G01S 15/00
[52] U.S. Cl. .................................... 367/137; 367/908
[58] Field of Search ................. 367/908, 13, 137, 138; 73/861.28

[56] References Cited

U.S. PATENT DOCUMENTS 3,693,445 9/1972 Johnson .............................. 367/908

OTHER PUBLICATIONS

Detection of Water Induction in Steam Turbines, Phase 3: Field Demonstration, Electric Power Research Institute (EPRI), Project 637-2, Final Report EPRI CS-4285, Sep. 1985.
Results of a Field Verification for a Turbine Water Induction Monitor, Presented at the EPRI Seminar on Fossil Plant Retrofits for Improved Heat Rate and Availability, Dec. 1-3, 1987 in San Diego, Calif.

Primary Examiner—Thomas H. Tarcza
Assistant Examiner—Daniel T. Pihulic
Attorney, Agent, or Firm—K. Bach

[57] ABSTRACT

A monitor for detecting the presence of liquid in a fluid supply conduit wherein the fluid has at least a liquid phase, and wherein bubbles may form in the fluid, is shown to include an ultrasonic signal transmitter for generating and transmitting an ultrasonic signal, an ultrasonic signal receiver, means for attaching the transmitter and receiver to the conduit, and a waveguide which confines a portion of the fluid so that the ultrasonic signal is guided to the receiver when liquid is present in the confined portion. The waveguide also tends to exclude bubbles from the confined portion. The waveguide may include a cylinder positioned in the conduit between the transmitter and the receiver and which has a plurality of openings to allow the ingress and egress of liquid.

20 Claims, 2 Drawing Sheets

LIQUID ACOUSTIC WAVEGUIDE TUBE

FIELD OF THE INVENTION

The present invention relates generally to the field of monitors and more particularly to the field of acoustic monitors used for the detection of liquid in a multiphase fluid supply line such as an extraction line in a steam turbine power plant.

BACKGROUND OF THE INVENTION

Although the present invention may be used in relation to various multiphase fluids, i.e. oil containing bubbles or other particles, in order to detect the presence of liquid in a supply line or other conduit, the invention will be described in relation to the detection of water induction in a steam operated power plant.

The induction of water or cool steam vapor onto turbine elements in a steam operated power plant can cause severe damage requiring immediate and costly repair, such as plastic deformation, broken blades, cylinder distortion and broken bolts. In most instances such damage is immediately recognizable and extremely costly to repair. Even if such damage is not of a degree rendering it immediately recognizable and thus requiring immediate repair, it nonetheless can be very costly in two respects. First, such damage will extend power plant down time for routine scheduled inspection and subsequent repair, and second such damage can cause a decrease in power plant performance. It has been estimated that over a twelve month period a decrease in performance of one third of one percent of a 500 MW power plant can cost $200,000.00. Consequently, there is a need for equipment which can detect water induction before an impending incident.

Detection of Water Induction in Steam Turbines, Phase 3: Field Demonstration, Electric Power Research Institute (EPRI), Project 637-2, Final Report EPRI CS-4285 dated September, 1985, describes various monitoring systems for detecting water induction in a steam operated power plant. One such system involved the use of temperature sensing devices, such as thermocouples, positioned in so-called thermocouple wells located along the length of supply lines from which induction might occur, for example an extraction line which leads to a low-pressure feedwater heater. A predetermined drop in line temperature would constitute an indication that water or cool steam vapor was present in the supply line. The problem with such monitors was in the response time associated with the thermocouples. For certain situations, thermocouples are too slow to provide adequate warning of an impending water-induction incident.

Another monitoring system described in the EPRI Report was said to utilize electronic liquid-level sensors to detect the presence of water in the subject supply lines. The problem with these monitors is the time delay exhibited due to piping flow restrictions.

A third type of monitoring system was described in the EPRI Report and was also described in Barton, Serge P., et al., Results of a Field Verific tion for a Turbine Water Induction Monitor, presented at the EPRI Seminar on Fossil Plant Retrofits for Improved Heat Rate and Availability, December 1–3, 1987 in San Diego, Calif. This third system described positioning an ultrasonic acoustic transmitter on one side of a turbine extraction line which leads to a low-pressure feedwater heater. An ultrasonic acoustic receiver was said to be positioned on the opposite side of the extraction line and in so called line-of-sight propagation alignment with the transmitter. The presence of water would enhance the transmission of a line-of-sight propagated signal to the receiver. In the absence of water, no line-of-sight signal would be received, although, a significantly smaller strength ultrasonic signal would still travel through the wall of the supply line to the receiver. Since the strength of the signal traveling through the wall is easily distinguishable from the line-of-sight signal, the presence or absence of water could be determined. The only delays associated with this type of system are those resulting from the generation, transmission, reception and processing of the ultrasonic signal. Such delays were said to be in an acceptable range in order to give adequate warning of an impending incident. Unfortunately, certain operational conditions were masked from detection by the ultrasonic monitoring system.

In normal operation, extraction lines and steam lines are conduits for vapor flow. At such times condensate in heaters and drain receivers are at or near their saturation temperatures. During rapid plant transients, such as when the load is rapidly reduced, a sudden drop in pressure in the feedwater heater can occur, lowering the saturation temperature of the feedwater, which in turn causes the immediate formation of steam bubbles at the vapor pressure of the liquid. The liquid enthalpy will be reduced by the heat of vaporization, e.g., bubble formation, until thermal equilibrium is restored. Since bubbles are being formed throughout the liquid, the bulk volume of the liquid increases. The increasing bulk volume results in the movement of liquid and bubbles to lower pressure regions of the power plant, i.e. back through one or more extraction lines into the turbine casing and rotating elements.

The presence of bubbles in a conduit incorporating the previously described ultrasonic monitor cause a scattering of the line-of-sight ultrasonic signal. As a result, the monitor does not sense the impending water induction incident. Consequently, a need exists for a monitoring system which exhibits the speed of the ultrasonic monitoring system and is capable of detecting a water induction incident in a supply or extraction line, despite the presence of bubbles.

SUMMARY OF THE INVENTION

It is an object of the present invention to provide a turbine system having a monitoring system which is capable of detecting water induction incidents quickly so that adequate warning can be given.

It is another object of the present invention to provide a monitoring system which is capable of detecting the presence of liquid in a fluid conduit.

It is still another object of the present invention to provide a monitoring system capable of detecting liquid in a fluid conduit when bubbles are present in the liquid.

It is a further object of the present invention to provide a monitoring system which incorporates ultrasonic signals in the detection of liquid in a fluid supply conduit.

It is still a further object of the present invention to provide a monitoring system which confines a portion of the fluid in a fluid conduit so that an ultrasonic signal may be guided from a transmitter to a receiver when liquid is present in the confined portion.

It is yet a further object of the present invention to provide a monitoring system which confines a portion of the fluid in a fluid conduit and which tends to exclude bubbles which may be present in the fluid from the confined portion.

These and other objects of the invention are achieved by a monitor for detecting the presence of liquid in a fluid conduit wherein the fluid has at least a liquid phase, and wherein bubbles may form in the fluid, which monitor includes an ultrasonic signal transmitter for generating and transmitting an ultrasonic signal, an ultrasonic signal receiver, means for attaching the transmitter and receiver to the conduit, and a waveguide which confines a portion of the fluid so that the ultrasonic signal is guided to the receiver when liquid is present in the confined portion. The waveguide also tends to exclude bubbles from the confined portion. The waveguide may include a cylinder positioned in the conduit between the transmitter and the receiver and which has a plurality of openings to allow the ingress and egress of liquid.

These and other objects and advantages of the invention will become more apparent from the following detailed description when taken in conjunction with the following drawings.

DETAILED DESCRIPTION OF THE PREFERRED EMBODIMENT

Figure 1:
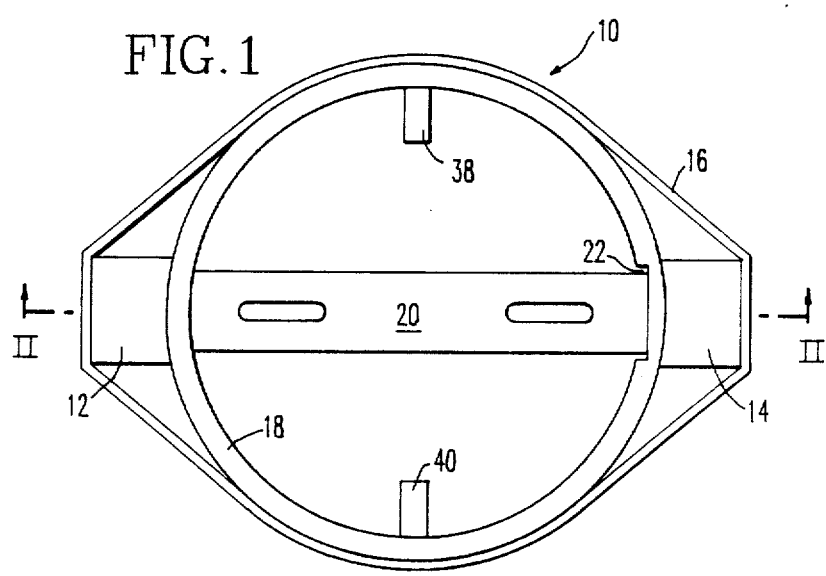
FIG. 1 is a plan view of the monitoring system of the present invention.

A new and novel system for monitoring the presence of liquid in a fluid conduit is shown in FIG. 1 and generally designated 10. An ultrasonic acoustic transmitter 12 and an ultrasonic acoustic receiver 14 are shown to be attached by strap 16 to opposite sides of fluid conduit 18. Conduit 18 should be metallic in order that the ultrasonic signal may be transmitted therethrough to receiver 14. If conduit 18 is not metallic, it will be necessary to insert a so-called acoustic window in conduit 18 at the point of attachment of transmitter 12 and receiver 14. Transmitter 12 and receiver 14 may be any known and available ultrasonic transmitter and receiver. Since such ultrasonic units are available, they have been shown in block form.

In the preferred embodiment, the ultrasonic transmitter and receiver are of the piezoelectric type, for example optimally matched transmitter-receiver pairs sold by Etalon Corporation of Indianapolis, Ind. In such devices a piezoelectric disk element having electrodes attached thereto is abutted on one side by an acoustic window and on another side by a damping element. A high voltage impulse applied to the electrodes shock excites the piezoelectric disk into damped mechanical resonance and emits a short ultrasonic pulse. In previous monitor systems, this pulse travels into the wall of the monitored conduit. If the conduit were filled with water, much of the ultrasonic signal would couple through the conduit wall into the water and travel to the opposite side of the conduit by line-of-sight propagation. After traveling across the conduit, the ultrasonic signal would again pass through the conduit wall to the receiver, whereupon it will be converted into an electrical signal. As indicated previously, the presence of bubbles would mask an impending incident.

Figure 2:
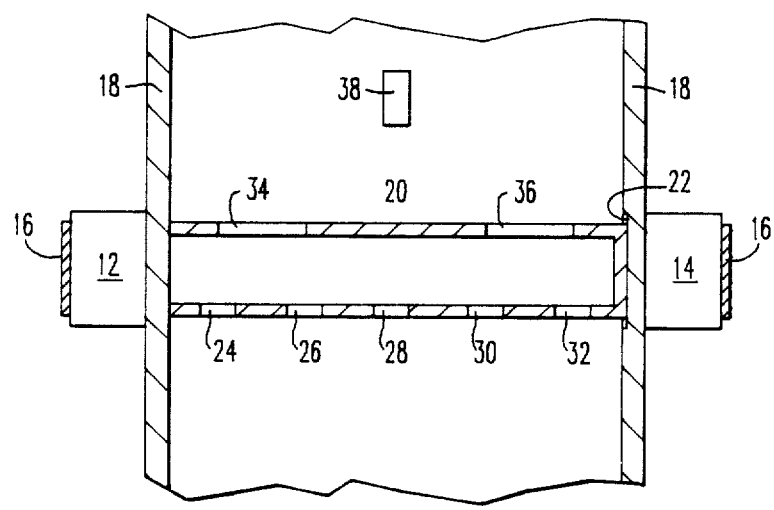
FIG. 2 is a section view taken along the line II—II of FIG. 1.

In order to detect liquid in conduit 18, even when mixed with bubbles, I have devised a way to confine a portion of the fluid passing through conduit 18 and detect the presence of liquid. This is achieved through the use of waveguide 20. In the preferred embodiment, waveguide 20 is a heavy wall tube of erosion resistant metal. As shown in FIG. 2, waveguide 20 is mounted within conduit 18 between transmitter 12 and receiver 14. Since it is important not to impose any stress on conduit 18, waveguide 20 is mounted to conduit 18 by securing the end proximate transmitter 12 by any suitable method, for example welding. The opposite end of waveguide 20 is positioned in a slip joint 22 formed in conduit 18 proximate receiver 14.

Openings 24-32 are provided for the ingress of fluid into waveguide 20. Openings or vents 34 and 36 are provided for the egress of fluid from waveguide 20. In the preferred embodiment the openings are slot shaped. The flow of fluid around waveguide 20 tends to streamline which has the effect of excluding bubbles from passing through openings 24 $\alpha$ 32. Consequently, there is a tendency for the waveguide to only confine any liquid which may be flowing in conduit 18. If, however, bubbles should become confined within waveguide 20, the line-of-sight propagation signal will still be directed to receiver 14 because the reflection of the signal from any bubbles will be directed into the liquid confined within waveguide 20 by the waveguide walls. Thereby, the ultrasonic signal reaches receiver 14 with minimum attenuation. Thus an impending water induction incident can be detected even if bubbles are present in fluid conduit 18.

Two thermocouple wells 38 and 40 are also shown in FIG. 1. The importance of showing these wells is to demonstrate that the monitoring system of the present invention is preferred to be positioned within a plane that does not include wells 38 and 40. Wells 38 and 40 have the tendency to interfere with the ultrasonic signal traveling in the walls of conduit 18 to receiver 14, the so-called wraparound signal. This wraparound signal may be utilized to maintain a minimum signal level in the monitoring system during use.

Figure 3:
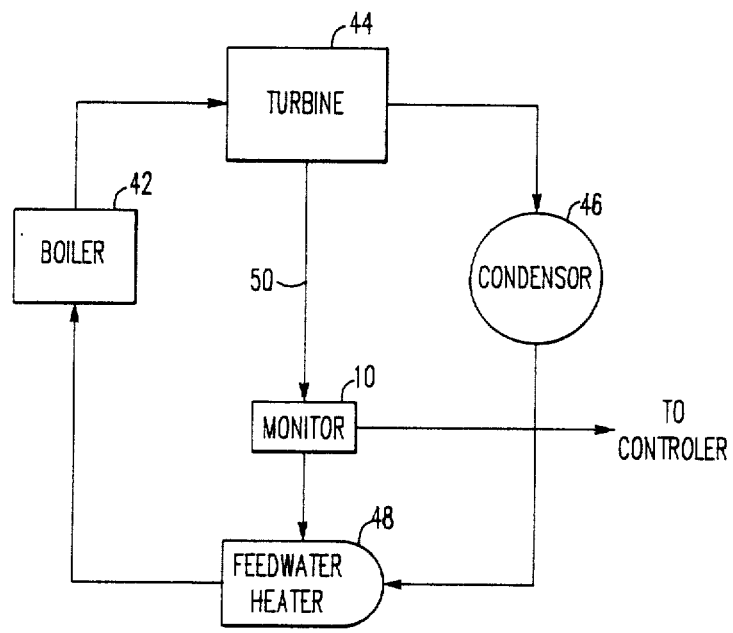
FIG. 3 is a diagrammatic view of a steam turbine system incorporating the monitoring system of the present invention.

Consider now the incorporation and operation of the above described monitoring system in the steam turbine system shown in FIG. 3. Steam is heated by a boiler 42 and provided under pressure to a turbine 44. Turbine 44 can include any steam turbine, for purposes of the present invention, or may include a number of interconnected turbines for example a power plant which includes a high pressure turbine, an intermediate pressure turbine and a low pressure turbine. For the purposes of illustration, assume that turbine 44 is a low pressure turbine. Steam exhausted from the turbine is presented to a condenser 46 where such steam is condensed into so-called feedwater. Before the feedwater is provided to boiler 42 for recirculation to turbine 44, the feedwater is first heated in feedwater heater 48. Heater 48 serves to raise the temperature of the feedwater to a desired level. In order to heat the feedwater in heater 48, a small amount of the steam supplied to turbine 44 is extracted and provided to heater 48 via an extraction line 50. Mounted on extraction line 50 is monitoring system 10.

As indicated previously, if during rapid plant transients, such as when the load on turbine 44 is rapidly reduced, a sudden drop in pressure in the feedwater heater can occur. This drop in pressure results in a lowering of the saturation temperature of the feedwater, which in turn causes the immediate formation of steam bubbles at the vapor pressure of the liquid. The liquid enthalpy of the feedwater will be reduced by the heat of vaporization, e.g., bubble formation, until thermal equilibrium is restored. Since bubbles are being formed throughout the liquid, the bulk volume of the liquid increases. The increasing bulk volume results in the movement of liquid and bubbles to lower pressure regions of the power plant, i.e. into and through extraction line 50 to turbine 44. Monitor 10 serves to detect the presence of liquid in the extraction line and through a signal provided to any appropriate controller, constitutes a means of determining an impending water induction incident.

As used herein the term multi-phase fluid refers not only to a single fluid such as water which can have liquid, gas and solid phases, but also to combinations of unrelated substances such as oil having air bubbles or other non-oil particles suspended or confined therein.

While the invention has been described and illustrated with reference to specific embodiments, those skilled in the art will recognize that modification and variations may be made without departing from the principles of the invention as described herein above and set forth in the following claims. For example the monitoring system of the present invention may be utilized as a flow monitor for any two-phase mixture where voids may exist.

What is claimed is:

1. A monitor for detecting the presence of a liquid phase in a multi-phase fluid conduit wherein said fluid has at least a liquid phase, and wherein a second phase may be present in said fluid, comprising, an ultrasonic signal transmitter for generating and transmitting an ultrasonic signal, an ultrasonic signal receiver, attachment means for attaching said transmitter and receiver to said conduit, and waveguide means for confining a portion of said fluid so that said ultrasonic signal is guided to said receiver when either said liquid phase or said second phase is present in said confined portion.

2. A monitor for detecting the presence of liquid in a fluid conduit wherein said fluid has at least a liquid phase, and wherein bubbles may form in said fluid, comprising, an ultrasonic signal transmitter for generating and transmitting an ultrasonic signal, an ultrasonic signal receiver, attachment means for attaching said transmitter and receiver to said conduit, and waveguide means for confining a portion of said fluid so that said ultrasonic, signal is guided to said receiver when either liquid or bubbles are present in said confined portion.

3. The monitor of claim 2, wherein bubbles are present in said fluid and wherein said waveguide means tends to exclude said bubbles from said confined portion so that primarily liquid is there confined.

4. The monitor of claim 3, wherein said ultrasonic signal when reflected by said bubbles is reflected back into said liquid by said waveguide means.

5. The monitor of claim 4, wherein said waveguide means comprises a cylinder positioned in said conduit between said transmitter and receiver such that one end of said cylinder is positioned proximate said receiver and the other end of said cylinder is positioned proximate said transmitter, said cylinder being provided with a plurality of openings along the length thereof for the ingress and egress of said fluid.

6. The monitor of claim 5, wherein said cylinder has at least one end attached to said conduit in a location proximate said transmitter.

7. The monitor of claim 5, wherein said openings are slot shaped.

8. The monitor of claim 2, wherein said transmitter and receiver are attached by said attachment means to opposite sides of said conduit.

9. A steam turbine system comprising:
a steam turbine;
boiler means, connected to the input of said turbine, for generating steam from preheated feedwater and for providing said steam to said turbine;
condenser means, connected to the output of said turbine, for condensing the steam which is exhausted from said turbine into feedwater;
feedwater heater means, connected between said condenser and said boiler, for preheating said feedwater from said condenser and for providing preheated feedwater to said boiler, wherein said feedwater is preheated through the use of steam;
steam extraction means, connected between said turbine and said feedwater heater means, for extracting a portion of the steam provided to said turbine and for providing the extracted steam to said feedwater heater means; and
a monitor, connected to said steam extraction means, for detecting the presence of feedwater in said steam extraction means, wherein bubbles may form in said feedwater, which monitor comprises, an ultrasonic signal transmitter for generating and transmitting an ultrasonic signal, an ultrasonic signal receiver, attachment means for attaching said transmitter and receiver to said steam extraction means, and waveguide means for confining a portion of the fluid in said steam extraction means so that said ultrasonic signal, is guided to said receiver when either feedwater or bubbles are present in said confined portion.

10. In a steam turbine system, wherein feedwater is preheated in a feedwater heater by steam extracted from the steam turbine and wherein a steam extraction line is provided between said steam turbine and said feedwater heater, a monitor for detecting the presence of feedwater in a said steam extraction line, and wherein bubbles may form in said feedwater, comprising, an ultrasonic signal transmitter for generating and transmitting an ultrasonic signal, an ultrasonic signal receiver, attachment means for attaching said transmitter and receiver to said steam extraction line, and waveguide means for confining a portion of the fluid within said steam extraction line so that said ultrasonic signal is guided to said receiver when either feedwater or bubbles are present in said confined portion.

11. The turbine system of claim 10, wherein bubbles are present in said feedwater and wherein said waveguide means tends to exclude said bubbles from said confined portion so that primarily feedwater is there confined.

12. The turbine system of claim 11, wherein said ultrasonic signal when reflected by said bubbles is reflected back into said feedwater by said waveguide means.

13. The turbine system of claim 12, wherein said waveguide means comprises a cylinder positioned in said steam extraction line between said transmitter and receiver such that one end of said cylinder is positioned proximate said receiver and the other end of said cylinder is positioned proximate said transmitter, said cylinder being provided with a plurality of openings along the length thereof for the ingress and egress of fluid.

14. The turbine system of claim 13, wherein said cylinder has at least one end attached to said conduit in a location proximate said transmitter.

15. The turbine system of claim 13, wherein said openings are slot shaped.

16. The turbine system of claim 10, wherein said transmitter and receiver are attached by said attachment means to opposite sides of said steam extraction line.

17. A method for detecting the presence of a liquid phase in a multi-phase fluid conduit wherein said fluid has at least a liquid phase, and wherein a second phase may be present in said fluid, comprising the steps of, attaching an ultrasonic signal transmitter to said fluid conduit for generating and transmitting an ultrasonic signal, attaching an ultrasonic signal receiver to said conduit, confining a portion of said fluid within said conduit and guiding said ultrasonic signal to said receiver when either said liquid phase is or said second phase present in the confined portion.

18. A method for detecting the presence of a liquid phase in a multi-phase fluid conduit wherein said fluid has at least a liquid phase, and wherein a second phase may be present in said fluid, comprising the steps of, transmitting an ultrasonic signal into said conduit from one side thereof, confining a portion of said fluid in said conduit, guiding said ultrasonic signal through said conduit when either said liquid phase is or said second phase present in said confined portion, and receiving the guided ultrasonic signal.

19. The method of claim 18, wherein bubbles are present in said liquid and further comprising the step of excluding said bubbles from said confined portion so that primarily liquid is there confined.

20. The method of claim 19, wherein said ultrasonic signal is reflected by said bubbles wherein said step of guiding said ultrasonic signal through said conduit further comprises the step of reflecting said ultrasonic signal back into said confined portion.

* * * * *